United States Patent
Sato et al.

(10) Patent No.: US 7,126,003 B2
(45) Date of Patent: Oct. 24, 2006

(54) METHOD FOR PRODUCING 2-AZETIDINONE DERIVATIVE

(75) Inventors: Kouji Sato, Edogawa-ku (JP); Tsutomu Yagi, Edogawa-ku (JP); Yutaka Kitagawa, Edogawa-ku (JP); Shigeru Ichikawa, Edogawa-ku (JP); Akihiro Imura, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 310 days.

(21) Appl. No.: 10/469,918

(22) PCT Filed: Mar. 4, 2002

(86) PCT No.: PCT/JP02/01969

§ 371 (c)(1), (2), (4) Date: Sep. 5, 2003

(87) PCT Pub. No.: WO02/070512

PCT Pub. Date: Sep. 12, 2002

(65) Prior Publication Data

US 2004/0072309 A1 Apr. 15, 2004

(30) Foreign Application Priority Data

Mar. 7, 2001 (JP) .............................. 2001-63840

(51) Int. Cl.
*C07D 401/04* (2006.01)
*C07D 205/04* (2006.01)

(52) U.S. Cl. .................... 546/268.1; 548/950; 548/952

(58) Field of Classification Search ................ 548/950, 548/952; 546/288.1
See application file for complete search history.

(56) References Cited

U.S. PATENT DOCUMENTS 5,567,614 A 10/1996 Patel et al.
5,811,292 A * 9/1998 Patel et al. .................. 435/280
5,879,929 A * 3/1999 Patel ........................... 435/280
6,548,293 B1 * 4/2003 Holton et al. ............... 435/280
6,677,456 B1 * 1/2004 Soga et al. ............... 546/284.1

FOREIGN PATENT DOCUMENTS

| CN | 1210535 A | 3/1999 |
|---|---|---|
| EP | 0 582 469 A2 | 9/1994 |
| EP | 933360 A1 | 8/1999 |
| EP | 1 001 036 A2 | 5/2000 |
| JP | 61-280295 A | 12/1986 |
| JP | 6-172276 A | 6/1994 |
| JP | 8-126493 A | 5/1996 |
| WO | WO 93/17997 A1 | 9/1993 |
| WO | WO 01/29245 A2 | 4/2001 |

OTHER PUBLICATIONS

Rosario Brieva et al., "Chemoenzymatic Synthesis of the C-13 Side Chain of Taxol: Optically-Active 3-Hydroxy-4-phenyl β-Lactam Derivatives", J. Org. Chem. (1993) vol. 58, No. 5, pp. 1068-1075.
Supplementary European Search Report dated Jan. 21, 2005.

* cited by examiner

*Primary Examiner*—Golam M. M. Shameem
(74) *Attorney, Agent, or Firm*—Sughrue Mion, PLLC

(57) ABSTRACT

A process for producing a compound represented by the following formula (II) which comprises treating a compound represented by the following formula (I) (wherein $R^1$, $R^2$ and $R^3$ represent each a specific substituent) with an enzyme capable of asymmetrically hydrolyzing an ester and the novel compound (II). The process of the present invention makes it possible to easily obtain an optically active 2-azetidinone derivative in a large amount at a low cost

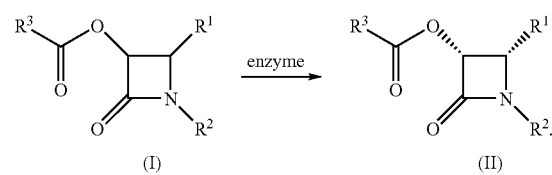

12 Claims, No Drawings

METHOD FOR PRODUCING 2-AZETIDINONE DERIVATIVE

TECHNICAL FIELD

This invention relates to a process for producing a 2-azetidinone derivative.

BACKGROUND ART

2-Azetidinone derivatives are important as reactive compounds for forming the subsituent at the 13-position of an anticancer compound having the following structure.

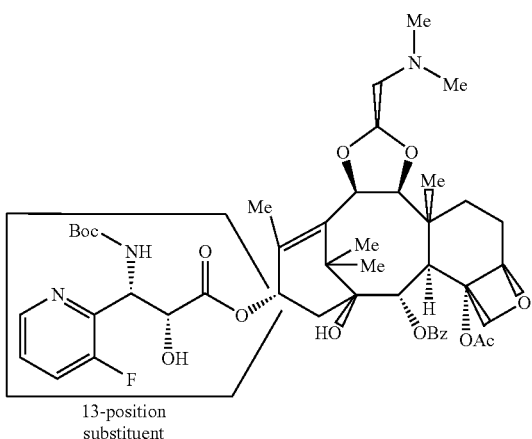

As such a reactive compound, use is made of, for example, a compound (1) having the following structure (TIPS: triisopropylsilyl group, Boc: tertiary butoxycarbonyl group (hereinafter "tertiary" will be abbreviated as "t-", i.e., "t-butoxycarbonyl group"))

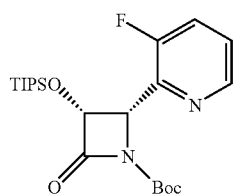

This compound (1) is obtained by subjecting a racemic compound (2) (PMP: paramethoxyphenyl group (4-methoxyphenyl group), Ac: acetyl group, the acetoxy group at the 3-position and the 3-fluoro-2-pyridyl group at the 4-position being in the cis-configuration):

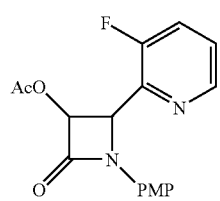

to deprotection of Ac at the 3-position, conversion into TIPS, recrystallization, elimination of PMP at the 1-position, and separation by column chromatography (which will be sometimes abbreviated as column hereinafter) to give: a compound (3):

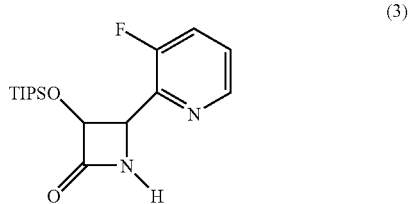

followed by separation with the use of an optical resolution column and attachment of a protective group.

The process for obtaining the compound (1) from the racemic compound (2) suffers from a problem that troublesome procedures (epimerization, replacement of the solvent for recrystallization, isolation by the column, etc.) are needed and yet only a low yield can be achieved. To obtain the compound (1), there arises an additional problem that the compound (3) should be separated by using an optical resolution column in the step prior to the final step, which results in an increase in the cost in case of mass production.

The present invention aims at providing a production process whereby an optically active 2-azetidinone derivative can be easily produced in a large amount at a low cost.

DISCLOSURE OF THE INVENTION

The present inventors have found a production process whereby an optically active 2-azetidinone derivative can be efficiently produced in a large amount at a low cost by treating a racemic 2-azetidinone derivative with an enzyme capable of asymmetrically hydrolyzing an ester, thereby completing the present invention.

Accordingly, the present invention relates to a process for producing a compound represented by formula (II):

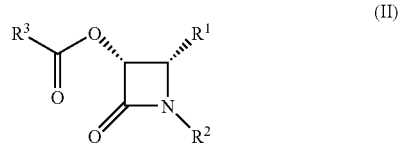

wherein $R^1$ represents a phenyl group or a pyridyl group (in which each group may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group); $R^2$ represents a hydrogen atom, a hydroxyl group, an alkoxyl group having 1 to 6 carbon atoms which may have substituent(s), an alkanoyl group having 1 to 6 carbon atoms which may have substituent(s), an alkenoyl group having 2 to 6 carbon atoms which may have substituent(s), an aryl group which may have substituent(s), an aryloyl group which may have substituent (s) or an aralkyl group which may have substituent(s); and $R^3$ represents an alkyl group having 1 to 6 carbon atoms which may have substituent(s) or an alkenyl group having 2 to 6 carbon atoms which may have substituent(s); which comprises treating a compound represented by formula (I) with an enzyme capable of asymmetrically hydrolyzing an ester:

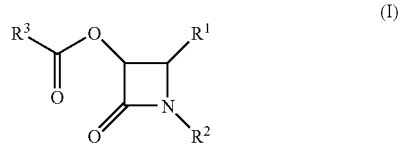

wherein $R^1$, $R^2$ and $R^3$ are each as defined above.

The present invention further relates to the followings:

The above-described production process wherein $R^1$ is a 3-fluoro-2-pyridyl group;

the above-described production process wherein $R^2$ is a a phenyl group (which may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group) or an aralkyl group (having a structure wherein an alkyl group having 1 to 6 carbon atoms is substituted by one or more aryl group(s); and said aryl moiety may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group);

the above-described production process; wherein $R^2$ is a 4-methoxyphenyl group or a bis (4-methoxyphenyl) methyl group;

the above-described production process wherein $R^3$ is a methyl group;

the above-described production process wherein the enzyme is a lipase;

the above-described production process wherein the lipase is a lipase originating in a microorganism belonging to the genus *Pseudomonas*;

the above-described production process wherein the lipase is a lipase originating in a microorganism belonging to the genus *Aspergillus*;

the above-described production process wherein the lipase is immobilized;

a compound represented by formula (II):

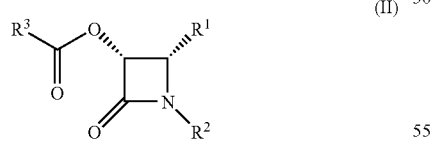

wherein $R^1$ represents a phenyl group or a pyridyl group (in which each group may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group); $R^2$ represents a hydrogen atom, a hydroxyl group; an alkoxyl group having 1 to 6 carbon atoms which may have substituent(s), an alkanoyl group having 1 to 6 carbon atoms which may have substituent(s), an alkenyl group having 2 to 6 carbon atoms which may have substituent(s), an aryl group which may have substituent(s), an aryloyl group which may have substituent(s) or an aralkyl group which may have substituent(s); and $R^3$ represents an alkyl group having 1 to 6 carbon atoms which may have substituent(s) or an alkenyl group having 2 to 6 carbon atoms which may have substituent(s);

the above-described compound wherein $R^1$ is a 3-fluoro-2-pyridyl group;

the above-described compound wherein $R^2$ is a phenyl group (which may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group) or an aralkyl group (having a structure wherein an alkyl group having 1 to 6 carbon atoms is substituted by one or more aryl group(s); and said aryl moiety may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group);

the above-described compound wherein $R^2$ is a 4-methoxyphenyl group or a bis(4-methoxyphenyl)methyl group;

the above-described compound wherein $R^3$ is a methyl group, etc.

In the present invention, the compound represented by formula (I) (which will be called the compound (I) hereinafter and the same will apply to compounds represented by other formulae) is treated with an enzyme capable of asymmetrically hydrolyzing an ester (which will be sometimes simply called an "enzyme" hereinafter) to thereby give the compound (II). Usually another compound (III) is formed together with the compound (II) as shown in the following reaction scheme.

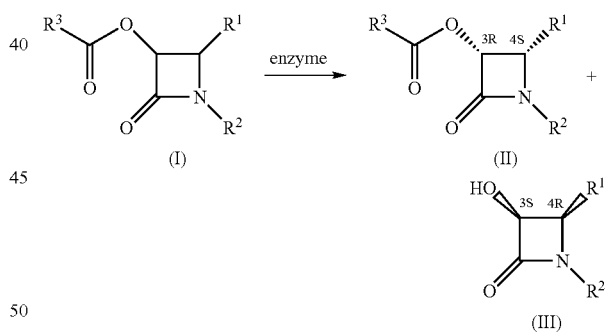

It is preferable herein that in the compound (I), the acyloxy group at the 3-position and $R^1$ at the 4-position are in the cis-configuration. In this case, the compound (I) is a racemate having the (3R, 4S) and (3S, 4R) forms, the compound (II) is in the (3R, 4S) form and the compound (III) is in the (3S, 4R) form. Since the (3S, 4R) form of the compound (I) is selectively ester-hydrolyzed by the enzyme the (3R, 4S) form of the compound (I), namely, the compound (II) selectively remains. In case where the compound (II) has crystalline nature, the compound (II) may be separated from the mixture of the compound (II) with the compound (III) by usual recrystallization using a suitable solvent without resort to a column. It is advantageous that, even though $R^3COO$ at the 3-position of the compound (II) is ester-hydrolyzed into OH and a desired protective group is introduced thereinto, the R-configuration at the 3-position and the S-configuration at the 4-position are sustained, and even though the amino group at the 1-position is eliminated or protected, the R-configuration at the 3-position and the S-configuration at the 4-psotion are sustained. Owing to these characteristics, the above-described compound (1) can be formed without resort to optical resolution by using a column, whereby an extremely high efficiency can be established (see, Examples and Referential Examples).

The enzyme to be used in the present invention is not particularly restricted, so long as it is capable of stereoselectively hydrolyzing the ester bond at the 3-position of the (3S, 4R) form of the compound (I).

A higher optical purity of the compound (III) obtained by the above-described reaction brings about the higher ester hydrolysis selectivity of the (3S, 4R) form of the compound (I). Therefore, it is favorable to employ such an enzyme.

It is preferable that the enzyme to be used in the present invention has an optical purity of the compound (III) of 80% ee or above, still preferably 90% ee or above and particularly preferably 95% ee or above.

As the enzyme to be used in the present invention, a lipase is preferable. It is still preferable to use a lipase originating in a microorganism, for example, a lipase originating in a microorganism belonging to the genus *Pseudomonas* or *Aspergillus*.

It is also preferable to use an immobilized lipase. Examples thereof include lipases immobilized on ceramics or diatomaceous earth.

As specific examples of the lipase, Amano PS, Amano PS-CI, Amano PS-DI and Amano AK (manufactured by Amano Enzyme), etc. may be cited.

To treat the compound (I) with the above-described enzyme, it is required to bring the compound (I) into contact with the enzyme. Although the contact method is not particularly restricted, it is preferable to dissolve the compound (I) in an appropriate solvent and then bring the enzyme into contact with the compound (I).

The contact time of bringing the above-described enzyme into contact with the compound (I) may be properly determined to achieve the desired hydrolysis ratio and optical purity. In the present invention, when an immobilized lipase is used as the enzyme, the reaction can proceed even if the contact time with the compound (I) is a short time. Illustratively, the contact time is preferably 0.5 to 48 hours, more preferably 0.5 to 24 hours, and most preferably 0.5 to 18 hours.

The solvent is not particularly restricted, so long as it would not inhibit the ester-hydrolysis reaction as described above. For example, use can be made of an organic solvent such as toluene, isopropyl ether, ethyl acetate, ethanol, acetonitrile, isopropyl ether, tetrahydrofuran, acetone, or a mixture thereof with water. In case of using a mixture of an organic solvent with water, it is preferable that the mixing ratio (by volume) of water is 5% or more but not more than 80%. In case of using ethanol as the organic solvent, the mixing ratio of water is preferably adjusted to 40%.

The reaction temperature may be properly determined depending on the solvent. Namely, the reaction temperature is preferably controlled to about 40° C. in case of using an ethyl acetate or toluene-based solvent, or to about 25° C. in case of using an ethanol-based solvent.

Stirring may be performed by using a stirrer, stirring blades, a shaker or the like. An adequate device may be suitably selected.

The relation between the concentration of the substrate, i.e., the compound (I) and the amount of the enzyme may be suitably controlled. In general, the selectivity of the enzyme would be lowered with an increase in the substrate concentration. Also, the selectively would be lowered with a decrease in the enzyme amount. It is preferable to control the substrate concentration to about 5% and the enzyme amount to about 0.4 (enzyme mass/substrate mass).

The pH of the reaction system is usually adjusted to the optimum pH value of the enzyme during the reaction. In the present invention, the initial pH value little differs from the pH value after the completion of the reaction. Thus, there arises a merit that no pH control is needed.

After the completion of the enzymatic reaction, the enzyme is filtered off and the solvent is concentrated under reduced pressure. Then the residue is extracted with a solvent, concentrated under reduced pressure and recrystallized from an appropriate solvent. Thus, the compound (II) can be obtained at a high purity (99% or above) and a high optical purity (99% ee or above).

Water-containing methanol is preferable as the solvent for crystallization. In particular, a methanol/water mixture (17:19 by volume) is preferable therefor.

The compound (II) thus obtained is a novel optically active compound.

In the compound (I) and the compound (II), the substituents $R^1$, $R^2$ and $R^3$ remain unchanged after the reaction.

Next, the substituents $R^1$, $R^2$ and $R^3$ will be illustrated in greater detail.

$R^1$ represents a phenyl group or a pyridyl group which may respectively have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group, preferably a halogen atom or an alkoxyl group.

It is particularly preferable that $R^1$ is a 3-fluoro-2-pyridyl group.

$R^2$ represents a hydrogen atom, a hydroxyl group, an alkoxyl group having 1 to 6 carbon atoms which may have substituent(s), an alkanoyl group having 1 to 6 carbon atoms which may have substituent(s), an alkenoyl group having 2 to 6 carbon atoms which may have substituent(s), an aryl group which may have substituent(s), an aryloyl group which may have substituent(s) or an aralkyl group which may have substituent(s).

It is preferable that $R^2$ is a phenyl group or an aralkyl group. The phenyl group may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group, preferably an alkoxyl group. The aralkyl group has a structure wherein an alkyl group having 1 to 6 carbon atoms is substituted by one or more aryl group(s), and the aryl moiety may have one or more Substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group.

It is particularly preferable that $R^2$ is a 4-methoxyphenyl group or a bis(4-methoxyphenyl)methyl group.

$R^3$ represents an alkyl group having 1 to 6 carbon atoms which may have substituent(s) or an alkenyl group having 2 to 6 carbon atoms which may have substituent(s). It is particularly preferable that $R^3$ is a methyl group.

BEST MODE FOR CARRYING OUT THE INVENTION

Now, the present invention will be described in greater detail by reference to the following Examples, but the present invention should not be construed as being limited thereto.

Optical purity was determined under the following conditions.

Column: ULTRON ES-OVM (150 mm×4.6 mmφ), Shinwa Kako
Mobile phase: MeOH:0.02M phosphate buffer pH 7.0=5:95
Flow rate: 1.0 ml/min
Temperature: 40° C.
Detection: 254 nm
Retention time: desired (3R, 4S) ester: 17 min, (3S, 4R) ester: 11 min, (3R, 4S) alcohol: 8.3 min, (3R, 4S) alcohol: 9.3 min, trans-alcohol: 11, 31 min

EXAMPLE 1

(3R, 4S)-cis-3-acetoxy-4-(3-fluoro-2-pyridyl)-1-(4-methoxyphenyl)-2-azetidinone

Cis-3-acetoxy-4-(3-fluoro-2-pyridyl)-1-(4-methoxyphenyl)-2-azetidinone (480 g) was suspended in a mixture of ethanol (5.76 l) with 0.1 M phosphate buffer pH 7.0 (3.84 l). Then an enzyme Lipase PS-CI (144 g) was added thereto and the mixture was stirred at 25° C. for 16 hours. After evaporating ethanol, the residue was extracted with methylene chloride and the organic layer was evaporated. To the obtained residue were added methanol (8.16 l) and water (9.18 l) and the mixture was stirred at 10° C. for 16 hours. The crystals thus precipitated were collected by filtration and dried under reduced pressure to thereby give the title compound (182 g, 99.7% ee) as pale brown crystals.

$^1$H-NMR (CDCl$_3$) δ: 1.80 (s, 3H), 3.74 (s, 3H), 5.72 (d, 1H, J=5.6 Hz), 6.09 (d, 1H, J=5.1 Hz), 6.77–6.83 (m, 2H), 7.21–7.29 (m, 2H), 7.30–7.33 (m, 1H), 7.41–7.46 (m, 1H), 8.43–8.46 (m, 1H)

EXAMPLE 1a (3R, 4S)-cis-3-acetoxy-4-(3-fluoro-2-pyridyl)-1-(4-methoxyphenyl)-2-azetidinone Cis-3-acetoxy-4-(3-fluoro-2-pyridyl)-1-(4-methoxyphenyl)-2-azetidinone (1 g) was suspended in a mixture of ethanol (6 ml) with 0.1 M phosphate buffer pH 7.0 (4 ml). Then an enzyme Lipase PS-CI (1 g) was added thereto and the mixture was stirred at 25° C. for 30 minutes. After evaporating ethanol, the residue was extracted with methylene chloride and the organic layer was evaporated. To the obtained residue were added methanol (17 ml) and water (19 ml) and the mixture was stirred at 10° C. for 16 hours. The crystals thus precipitated were collected by filtration and dried under reduced pressure to thereby give the title compound (400 mg, 99.9% ee) as pale brown crystals. The $^1$H-NMR data of this product was identical with those of the compound obtained in Example 1.

EXAMPLES 2 TO 14

Reactions were carried out as in Example 1 but employing different enzymes and reaction solvents in the asymmetric hydrolysis reaction.

TABLE 1

| Ex. | Enzyme | Reaction Solvent (water content: 5%) | Optical Purity of Compound (III) (% ee) | Reaction Ratio |
|---|---|---|---|---|
| 2 | Amano PS | toluene | >95 | >48 |
| 3 | Amano PS | isopropyl ether | 92 | 42 |
| 4 | Amano PS-CI | ethyl acetate | >95 | >48 |
| 5 | Amano PS-CI | toluene | >95 | >48 |
| 6 | Amano PS-CI | ethanol | >95 | >48 |
| 7 | Amano PS-CI | acetonitrile | >95 | 36 |
| 8 | Amano PS-CI | isopropyl ether | 93 | 32 |
| 9 | Amano PS-CI | tetrahydrofuran | >95 | 37 |
| 10 | Amano PS-CI | acetone | 93 | 29 |
| 11 | Amano PS-DI | toluene | 93 | 26 |
| 12 | Amano PS-DI | ethanol | 93 | 22 |
| 13 | Amano PS-DI | isopropyl ether | 91 | 28 |
| 14 | Amano AK | isopropyl ether | 91 | 35 |

EXAMPLE 15

(3R,4S)-cis-3-acetoxy-4-(3-fluoro-2-pyridyl)-1-{bis(4-methoxyphenyl)methyl}-2-azetidinone Cis-3-acetoxy-4-(3-fluoro-2-pyridyl)-1-{bis(4-methoxyphenyl)methyl}-2-azetidinone (200 mg) was suspended in a mixture of N,N-dimethylformamide (2 ml) with 0.1 M phosphate buffer pH 7.0 (18 ml). Then an enzyme Lipase PS-CI (200 mg) was added thereto and the mixture was stirred at 25° C. for 2 days. Then the liquid reaction mixture was extracted with methylene chloride. The organic layer was washed with water and dried over anhydrous magnesium sulfate. After evaporating the solvent, the obtained residue was subjected to silica gel column to thereby give the title compound (90 mg, 99.7% ee) as a colorless oily product. Also, (3S,4R)-cis-3-hydroxy-4-(3-fluoro-2-pyridyl)-1-{bis(4-methoxyphenyl)methyl}-2-azetidinone (96 mg, 99.5% ee) was obtained.

$^1$H-NMR (CDCl$_3$) δ: 1.75 (s, 3H), 3.72 (s, 3H), 3.79 (s, 3H), 5.30 (d, 1H, J=5 Hz), 5.91 (s, 1H), 5.93 (d, 1H, J=5 Hz), 6.64 (d, 2H, J=8.9 Hz), 6.83 (d, 2H, J=8.9 Hz), 7.06–7.20 (m, 6H), 8.35–8.42 (m, 1H)

Referential Example 1

N-[(E)-(3-fluoro-2-pyridyl)methylidene]-4-methoxyaniline

3-Fluoro-2-formylpyridine (229 g) and paraanisidine (225 g) were dissolved in toluene (2.29 l). After adding anhydrous sodium sulfate (334 g), the mixture was stirred at room temperature for 1 hour. After filtering off the insoluble matters, the liquid reaction mixture was concentrated under reduced pressure to thereby give the title compound (449 g).

$^1$H-NMR (CDCl$_3$) δ: 3.85 (s, 3H), 6.96 (d, J=8.9 Hz, 2H), 7.41 (d, J=8.9 Hz, 2H), 7.36–7.43 (m, 1H), 7.53 (m, 1H), 8.62 (d, J=4.3 Hz, 1H), 8.86 (s, 1H)

Referential Example 2

Cis-3-acetoxy-4-(3-fluoro-2-pyridyl)-1-(4-methoxyphenyl)-2-azetidinone

A solution (2.29 l) of N-[(E)-(3-fluoro-2-pyridyl)methylidene]-4-methoxyaniline (449 g) and triethylamine (204 g) in dichloromethane was cooled to −10° C. Then acetoxyacetyl chloride (250 g) was added dropwise thereinto and the resultant mixture was stirred at the same temperature for 30 minutes. Then it was heated to room temperature and stirred for 16 hours. The liquid reaction mixture was washed with water and the solvent was concentrated under reduced pressure to thereby give a crude product (723 g). This crude product was recrystallized from a solvent mixture of ethanol (6.9 l) and ethyl acetate (350 ml) to thereby give the title compound (486 g) as brown crystals.

$^1$H-NMR (CDCl$_3$) δ: 1.80 (s, 3H), 3.74 (s, 3H), 5.72 (d, 1H, J=5.6 Hz), 6.09 (d, 1H, J=5.1 Hz), 6.77–6.83 (m, 2H), 7.21–7.29 (m, 2H), 7.30–7.33 (m, 1H), 7.41–7.46 (m, 1H), 8.43–8.46 (m, 1H).

Referential Example 3

Cis-3-acetoxy-4-(3-fluoro-2-pyridyl)-1-{bis(4-methoxyphenyl)methyl}-2-azetidinone Under a nitrogen gas stream, 3-fluoro-2-formylpyridine (6.2 g) and bis(4-methoxyphenyl)methylamine (12 g) were dissolved in toluene (30 ml). After adding anhydrous sodium sulfate (12 g), the resultant mixture was stirred at room temperature for 30 minutes. After filtering off the insoluble matters, the liquid reaction mixture was concentrated under reduced pressure to give an imine compound. A solution (60 ml) of the imine compound thus obtained and triethylamine (8.2 ml) in dichloromethane was cooled to −5° C. Then acetoxyacetyl chloride (6.3 ml) was added dropwise thereinto and the resultant mixture was stirred at the same temperature for 30 minutes. Then it was heated to room temperature and stirred for 16 hours. The liquid reaction mixture was washed with water and then extracted with chloroform. The organic layers were combined, washed with water and dried over anhydrous magnesium sulfate. After concentrating the solvent under reduced pressure, ethyl acetate (20 ml) and diisopropyl ether (60 ml) were added to the obtained residue. The resultant mixture was stirred at room temperature. The crystals thus precipitated were collected by filtration to thereby give the title compound (21.8 g) as white crystals.

$^1$H-NMR (CDCl$_3$) δ: 1.75 (s, 3H), 3.72 (s, 3H), 3.79 (s, 3H), 5.30 (d, 1H, J=5 Hz), 5.91 (s, 1H), 5.93 (d, 1H, J=5 Hz), 6.64 (d, 2H, J=8.9 Hz), 6.83 (d, 2H, J=8.9 Hz), 7.06–7.20 (m, 6H), 8.35–8.42 (m, 1H)

Referential Example 4

(3R, 4S)-cis-3-hydroxy-4-(3-fluoro-2-pyridyl)-1-(4-methoxyphenyl)-2-azetidinone (3R,4S)-cis-3-acetoxy-4-(3-fluoro-2-pyridyl)-1-(4-methoxyphenyl)-2-azetidinone (181 g, 99.7% ee) was dissolved in a solvent mixture of methylene chloride (725 ml) and methanol (725 ml). After adding potassium carbonate (5.43 g) at 0° C., the resultant mixture was stirred at the same temperature for 1 hour. Then Dowex 50 (27 g) was added to the liquid reaction mixture followed by stirring. After filtering off the insoluble matters, the solvent was evaporated. Then toluene was added to the obtained residue and the mixture was azeotropically distilled. Thus, the title compound (157.9 g, 99.7% ee) was obtained as white crystals.

$^1$H-NMR (CDCl$_3$) δ: 3.74 (s, 3H), 5.34 (d, 1H, J=5 Hz), 5.62 (dd, 1H, J=5, 1 Hz), 6.78–6.81 (m, 2H), 7.15–7.38 (m, 3H), 7.52–7.59 (m, 1H), 8.45–8.47 (m, 1H)

Referential Example 5

(3R, 4S)-cis-4-(3-fluoro-2-pyridyl)-1-(4-methoxyphenyl)-3-triisopropylsilyloxy-2-azetidinone (3R,4S)-cis-3-hydroxy-4-(3-fluoro-2-pyridyl)-1-(4-methoxyphenyl)-2-azetidinone (126.5 g, 99.7% ee) was dissolved in methylene chloride (1.45 l). After adding triisopropylsilyl chloride (118 g) and imidazole (75 g), the resultant mixture was stirred at room temperature for 12 hours. After washing with water, the liquid reaction mixture was dried over anhydrous magnesium sulfate. Then the solvent was evaporated and n-hexane was added to the obtained residue. The mixture was stirred at room temperature for 2 hours and then at 0° C. for 2 hours. The crystals thus precipitated were collected by filtration. Thus, the title compound (176 g, 99.7% ee) was obtained as white crystals.

$^1$H-NMR (CDCl$_3$) δ: 0.91–1.06 (m, 21H), 3.74 (s, 3H), 5.38 (d, 1H, J=5.1 Hz), 5.50 (d, 1H, J=4.9 Hz), 6.78–6.81 (m, 2H), 7.23–7.30 (m, 3H), 7.35–7.39 (m, 1H), 8.41–8.43 (m, 1H).

Referential Example 6

(3R, 4S)-cis-3-hydroxy-4-(3-fluoro-2-pyridyl)-1-{bis(4-methoxyphenyl)methyl}-2-azetidinone (3R,4S)-cis-3-acetoxy-4-(3-fluoro-2-pyridyl)-1-{bis(4-methoxyphenyl)methyl}-2-azetidinone (90 mg, 99.5.% ee) was dissolved in a solvent mixture of tetrahydrofuran (0.3 ml), methanol (0.3 ml) and methylene chloride (0.3 ml). After adding potassium carbonate (2.3 mg), the resultant mixture was stirred at 0° C. for 1 hour and 30 minutes. Then Dowex 50 (10 mg) was added to the liquid reaction mixture followed by stirring for 5 minutes. After filtering off the insoluble matters, the solvent was evaporated. Thus, the title compound (81.6 mg, 99.5% ee) was obtained as a colorless oily product.

$^1$H-NMR (CDCl$_3$) δ: 3.70 (s, 3H), 3.81 (s, 3H), 5.08–5.27 (m, 2H), 5.94 (s, 1H), 6.55 (d, 2H, J=8.6 Hz), 6.85 (d, 2H, J=8.6 Hz), 7.15–7.20 (m, 6H), 8.36–8.41 (m, 1H)

Referential Example 7

(3R, 4S)-cis-4-(3-fluoro-2-pyridyl)-1-{bis(4-methoxyphenyl)methyl}-3-triisopropylsilyloxy-2-azetidinone (3R,4S)-cis-3-hydroxy-4-(3-fluoro-2-pyridyl)-1-(bis(4-methoxyphenyl)methyl)-2-azetidinone (81.6 mg, 99.5% ee) was dissolved in methylene chloride (1 ml). After adding triisopropylsilyl chloride (55.3 μl) and imidazole (20.4 mg), the resultant mixture was stirred at room temperature for 16 hours. After washing with water, the liquid reaction mixture was dried over anhydrous magnesium sulfate. Then the solvent was evaporated. Thus, the title compound (112.8 mg, 99.5% ee) was obtained as a colorless oily product.

$^1$H-NMR (CDCl$_3$) δ: 0.62–1.00 (m, 21H), 3.69 (s, 3H), 3.78 (s, 3H), 5.15 (d, 1H, J=5 Hz), 5.29 (d, 2H, J=5 Hz), 5.93

(s, 1H), 6.62 (d, 2H, J=8.6 Hz), 6.84 (d, 2H, J=8.6 Hz), 7.05–7.19 (m, 3H), 8.31–8.34 (m, 1H)

Referential Example 8

(3R, 4S)-cis-4-(3-fluoro-2-pyridyl)-3-triisopropylsilyloxy-2-azetidinone (3R,4S)-cis-4-(3-fluoro-2-pyridyl)-1-(4-methoxyphenyl)-3-triisopropylsilyloxy-2-azetidinone (167 g, 99.7% ee) was dissolved in acetonitrile (5 l) and then cooled to −10° C. After adding an aqueous solution. (5 l) of ammonium cerium nitrate (515 g), the resultant mixture was stirred at the same temperature for 30 minutes. After adding diisopropyl ether, the liquid reaction mixture was washed with water, a 4% aqueous sodium thiosulfate solution and a 2% aqueous sodium hydrogencarbonate solution. After evaporating the solvent, the obtained residue was dissolved in methanol (1.67 l). Then active carbon (167 g) was added and the resultant mixture was stirred at room temperature for 16 hours. After filtering off the active carbon, the solvent was evaporated. To the obtained residue were added ethanol (835 ml) and water (1.25 l). Then the mixture was stirred at room temperature for 5 hours. The crystals thus precipitated were collected by filtration to thereby give the title compound (97.5 g, 99.7% ee) as white crystals.

$^1$H-NMR (CDCl$_3$) δ: 0.89–1.08 (m, 21H), 5.71 (dd, 1H, J=4.8, 1.4 Hz), 5.35 (dd, 1H, J=4.9, 1.5 Hz), 6.18 (brs, 1H), 7.22–7.26 (m, 1H), 7.33–7.41 (m, 1H), 8.42–8.44 (m, 1H)

Referential Example 9

(3R, 4S)-cis-4-(3-fluoro-2-pyridyl)-3-triisopropylsilyloxy-2-azetidinone (3R,4S)-cis-4-(3-fluoro-2-pyridyl)-1-{bis(4-methoxyphenyl)methyl}-3-triisopropylsilyloxy-2-azetidinone (112.8 mg, 99.5% ee) was dissolved in acetonitrile (0.56 ml) and then cooled to −10° C. After adding an aqueous solution (4 ml) of ammonium cerium nitrate (346 mg), the resultant mixture was stirred at the same temperature for 30 minutes. After adding chloroform, the liquid reaction mixture was washed with water and dried over anhydrous magnesium sulfate. After evaporating the solvent, the obtained residue was subjected to silica gel column chromatography to thereby give the title compound (59.2 mg, 99.5% ee) as white crystals. The $^1$H-NMR data of this product was identical with those obtained in Referential Example 8.

Referential Example 10

(3R, 4S)-cis-1-(t-butoxycarbonyl)-4-(3-fluoro-2-pyridyl)-3-triisopropylsilyloxy-2-azetidinone (3R,4S)-cis-4-(3-fluoro-2-pyridyl)-3-triisopropylsilyloxy-2-azetidinone (44.9 g, 99.7% ee) was dissolved in tetrahydrofuran (448.6 ml). After adding 4-dimethylaminopyridine (1.62 g) and di-t-butyl dicarbonate (36.5 ml) at room temperature, the resultant mixture was stirred at the same temperature for 1 hour. After adding n-hexane, the liquid reaction mixture was washed with a 4% aqueous sodium hydrogencarbonate solution and water. The organic layer was dried over anhydrous magnesium sulfate. After evaporating the solvent, the title compound (58.1 g, 99.7% ee) was obtained as a brown oily product.

$^1$H-NMR (CDCl$_3$)δ: 0.88–1.02 (21H, m), 1.44 (9H, s), 5.27 (1H, d, J=5.6 Hz), 5.45 (1H, d, J=5.6 Hz), 7.23–7.28 (1H, m), 7.34–7.41 (1H, m), 8.41–8.44 (1H, m)

INDUSTRIAL APPLICABILITY

According to the present invention, an optically active compound (II) can be obtained from a racemic compound (I) merely by treating the compound (I) with an enzyme capable of asymmetrically hydrolyzing an ester. Thus, the process of the present invention makes it possible to efficiently obtain the compound (II) in a large amount at a low cost.

The invention claimed is:

1. A process for producing a compound represented by formula (II):

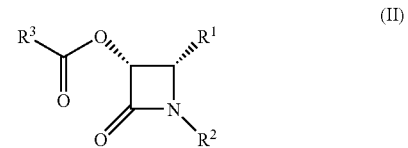

wherein $R^1$ represents a 3-fluoro-2-pyridyl group; R2 represents a hydrogen atom, a hydroxyl group, an alkoxyl group having 1 to 6 carbon atoms which may have substituent(s), an alkanoyl group having 1 to 6 carbon atoms which may have substituent(s), an alkenoyl group having 2 to 6 carbon atoms which may have substituent(s), an aryl group which may have substituent(s), an aryloyl group which may have substituent(s) or an aralkyl group which may have substituent(s); and R3 represents an alkyl group having 1 to 6 carbon atoms which may have substituent(s) or an alkenyl group having 2 to 6 carbon atoms which may have substituent(s);

which comprises treating a compound represented by formula (I) with an enzyme capable of asymmetrically hydrolyzing an ester:

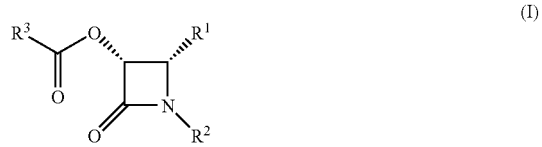

wherein $R^1$, $R^2$ and $R^3$ are each as defined above.

2. The process according to claim 1 wherein $R^2$ is a phenyl group (which may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group) or an aralkyl group (having a structure wherein an alkyl group having 1 to 6 carbon atoms is substituted by one or more aryl group(s); and said aryl moiety may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group).

3. The process according to claim 1 wherein $R^2$ is a 4-methoxyphenyl group or a bis(4-methoxyphenyl)methyl group.

4. The process according to claim 1 wherein $R^3$ is a methyl group.

5. The process according to claim 1 wherein the enzyme is a lipase.

6. The process according to claim 5 wherein the lipase is a lipase originating in a microorganism belonging to the genus Pseudomonas.

7. The process according to claim 5 wherein the lipase is a lipase originating in a microorganism belonging to the genus Aspergillus.

8. The process according to claim 6 or 7 wherein the lipase is immobilized.

9. A compound represented by formula (II):

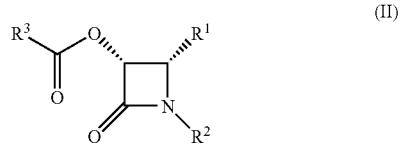

wherein $R^1$ represents a 3-fluoro-2-pyridyl group; $R^2$ represents a hydrogen atom, a hydroxyl group, an alkoxyl group having 1 to 6 carbon atoms which may have substituent(s), an alkanoyl group having 1 to 6 carbon atoms which may have substituent(s), an alkenoyl group having 2 to 6 carbon atoms which may have substituent(s), an aryl group which may have substituent(s), an aryloyl group which may have substituent(s) or an aralkyl group which may have substituent(s); and $R^3$ represents an alkyl group having 1 to 6 carbon atoms which may have substituent(s) or an alkenyl group having 2 to 6 carbon atoms which may have substituent(s).

10. The compound according to claim 9 wherein $R^2$ is a phenyl group (which may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group) or an aralkyl group (having a structure wherein an alkyl group having 1 to 6 carbon atoms is substituted by one or more aryl group(s); and said aryl moiety may have one or more substituent(s) selected from the group consisting of a halogen atom, an alkyl group having 1 to 6 carbon atoms, a halogenoalkyl group having 1 to 6 carbon atoms, an alkoxyl group having 1 to 6 carbon atoms, a nitro group, a carbamoyl group and a cyano group).

11. The compound according to claim 9 wherein $R^2$ is a 4-methoxyphenyl group or bis(4-methoxyphenyl)methyl group.

12. The compound according to claim 9 wherein $R^3$ is a methyl group.

* * * * *

UNITED STATES PATENT AND TRADEMARK OFFICE
CERTIFICATE OF CORRECTION

PATENT NO.        : 7,126,003 B2                                    Page 1 of 1
APPLICATION NO.   : 10/469918
DATED             : October 24, 2006
INVENTOR(S)       : Kouji Sato et al.

It is certified that error appears in the above-identified patent and that said Letters Patent is hereby corrected as shown below:

Please replace the figure representing formula (I) with the following figure located at column 12, lines 37 and 45.

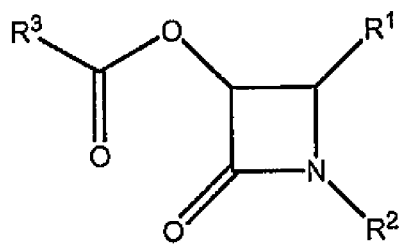

At column 12, line 21 please amend as follows:

wherein $R^1$ represents a 3-fluoro-2-pyridyl group; ~~R2~~ $R^2$

At column 12, line 30 please amend as follows:

stituent(s); and ~~R3~~ $R^3$ represents an alkyl group having 1

Signed and Sealed this

Twenty-third Day of October, 2007

JON W. DUDAS
*Director of the United States Patent and Trademark Office*